(12) United States Patent
Chen et al.

(10) Patent No.: US 8,741,562 B2
(45) Date of Patent: Jun. 3, 2014

(54) METHOD OF DETECTING ETHYLATED THYMIDINE DNA ADDUCTS

(71) Applicant: National Chung Cheng University, Chia-Yi (TW)

(72) Inventors: Hauh-Jyun Candy Chen, Chia-Yi (TW); Yi-Ching Wang, Tainan (TW); Wen-Peng Lin, Yilan County (TW)

(73) Assignee: National Chung Cheng University, Chia-Yi (TW)

( * ) Notice: Subject to any disclaimer, the term of this patent is extended or adjusted under 35 U.S.C. 154(b) by 84 days.

(21) Appl. No.: 13/664,020

(22) Filed: Oct. 30, 2012

(65) Prior Publication Data

US 2013/0295558 A1 Nov. 7, 2013

(30) Foreign Application Priority Data

May 7, 2012 (TW) .............................. 101116254 A

(51) Int. Cl.
*C12Q 1/68* (2006.01)
(52) U.S. Cl.
USPC ....................................................... 435/6.1
(58) Field of Classification Search
None
See application file for complete search history.

(56) References Cited

PUBLICATIONS

Zhang, F. et al. "Quantitation of DNA Adduct of Thymidylyl(3'-5') Thymidine Methyl Phosphotriester by Liquid Chromatography/ Negative Electrospray Tandem Mass Spectrometry" *Rapid Communications in Mass Spectrometry*, 2005, 19:2767-2772.
Chen H.C., et al. "Simultaneous Quantification of Three Lipid Peroxidation-Derived Etheno Adducts in Human DNA by Stable Isotope Dilution Nanoflow Liquid Chromatography Nanospray Ionization Tandem Mass Spectrometry" *Analytical Chemistry*, Jun. 1, 2010, 82(11):4486-4493.
Vineis, P. et al. "DNA adducts as markers of exposure to carcinogens and risk of cancer" *International Journal of Cancer*, Nov. 1, 2000, 88(3):325-328.
Thompson, C.L. et al. "Relationships among Benzo(α)pyrene Metabolism, Benzo(α)pyrene-diol-epoxide:DNA Adduct Formation, and Sister Chromatid Exchanges in Human Lymphocytes from Smokers and Nonsmokers" *Cancer Research*, Dec. 1, 1989, 49(23):6503-6511.
Hecht, S.S. "DNA adduct formation from tobacco-specific N-nitrosamines" *Fundamental and Molecular Mechanisms of Mutagenesis*, Mar. 8, 1999, 424(1-2):127-142.
Kang, H.I. et al. "Detection of $O^6$-methylguanine, $O^4$-methylthymine and $O^4$-ethylthymine in human liver and peripheral blood leukocyte DNA" *Carcinogenesis*, Jun. 1995, 16(6):1277-1280.
Godschalk, R. et al. "Comparison of multiple DNA adduct types in tumor adjacent human lung tissue: effect of cigarette smoking" *Carcinogenesis*, Dec. 2002, 23(12):2081-2086.
Godschalk, R. et al. "Modified Immunoenriched $^{32}$P-HPLC Assay for the Detection of $O^4$-Ethylthymidine in Human Biomonitoring Studies" *Chemical Research in Toxicology*, Mar. 2002, 15(3):433-437.
Eberle, G. et al. "Monoclonal antibodies for the specific detection of 3-alkyladenines in nucleic acids and body fluids" *Carcinogenesis*, Oct. 1990, 11(10):1753-1759.
Prevost, V. et al. "Immunoaffinity purification and gas chromatography—mass spectrometric quantification of 3-alkyladenines in urine: metabolism studies and basal excretion levels in man" *Carcinogenesis*, Feb. 1993, 14(2):199-204.
Kopplin, A. et al. "Urinary excretion of 3-methyladenine and 3-ethyladenine after controlled exposure to tobacco smoke" *Carcinogenesis*, Nov. 1995, 16(11):2637-2641.
Prevost, V. et al. "Cigarette Smoking and Urinary 3-Alkyladenine Excretion in Man" *Chemical Research in Toxicology*, Feb. 29, 1996, 9(2):439-444.
Chao, M.R. et al. "Quantitative determination of urinary N7-ethylguanine in smokers and non-smokers using an isotope dilution liquid chromatography/tandem mass spectrometry with on-line analyte enrichment" *Carcinogenesis*, Jan. 2006, 27(1):146-151.
Chen, L. et al. "Liquid Chromatography-Electrospray Ionization Tandem Mass Spectrometry Analysis of 7-Ethylguanine in Human Liver DNA" *Chemical Research in Toxicology*, Oct. 2007, 20(10)1498-1502.
Anna, L. et al. "Smoking-related $O^4$-ethylthymidine formation in human lung tissue and comparisons with bulky DNA adducts" *Mutagenesis*, Jul. 2011, 26(4):523-527.
Singh, R. et al. "Detection and Characterization of Two Major Ethylated Deoxyguanosine Adducts by High Performance Liquid Chromatography, Electrospray Mass Spectrometry, and $^{32}$P-Postlabeling. Development of an Approach for Detection of Phosphotriesters" *Chemical Research in Toxicology*, Jan. 1997, 10(1):70-77.
Haglund, J. et al. "Analysis of DNA-Phosphate Adducts In Vitro Using Miniaturized LC-ESI-MS/MS and Column Switching: Phosphotriesters and Alkyl Cobalamins" *Journal of the American Society for Mass Spectrometry*, Apr. 2004, 15(4):593-606.
Swann, P.F. "Why do $O^6$-alkylguanine and $O^4$-alkylthymine miscode? The relationship between the structure of DNA containing $O^6$-alkylguanine and $O^4$-alkylthymine and the mutagenic properties of these bases" *Mutation Research*, Nov.-Dec. 1990, 233(1-2):81-94.
Swenberg, J.A. et al. "$O^4$-Ethyldeoxythymidine, but not $O^6$-ethyldeoxyguanosine, accumulates in hepatocyte DNA of rats exposed continuously to diethylnitrosamine" *Proceedings of the National Academy of Sciences*, Mar. 15, 1984, 81(6):1692-1695.

(Continued)

*Primary Examiner* — James Martinell
(74) *Attorney, Agent, or Firm* — Saliwanchik, Lloyd & Eisenschenk

(57) ABSTRACT

A method of analyzing ethylated thymidine DNA adducts is disclosed. The method comprises the steps of: providing leukocyte DNA; adding at least one isotope-labeled internal standard and a plurality of enzymes to the leukocyte DNA, and hydrolyzing the leukocyte DNA into a plurality of nucleosides; using a solid-phase extraction column to extract the plurality of nucleosides; and using a stable isotope dilution nanoflow liquid chromatography-nanospray ionization tandem mass spectrometry to detect and quantify at least one ethylated thymidine DNA adduct in the plurality of extracted nucleosides.

10 Claims, 13 Drawing Sheets

(56) References Cited

PUBLICATIONS

Scherer, E. et al. "Formation by Diethylnitrosamine and Persistence of $O^4$-Ethylthymidine in Rat Liver DNA in Vivo" *Cancer Letters*, Jul. 1980, 10(1):1-6.

Engelse, L.D. et al. "$O^2$-and $O^4$-ethylthymine and the ethylphosphotriester dTp(Et)dT are highly persistent DNA modifications in slowly dividing tissues of the ethylnitrosourea-treated rat" *Carcinogenesis*, Jun. 1987, 8(6):751-757.

Thomale, J. et al. "Repair of $O^6$-ethylguanine in DNA protects rat 208F cells from tumorigenic conversion by *N*-ethyl-*N*-nitrosourea" *Proceedings of the National Academy of Sciences*, Dec. 15, 1990, 87(24):9883-9887.

Bronstein, S.M. et al. "Efficient Repair of $O^6$-Ethylguanine, but not $O^4$-Ethylthymine or $O^2$-Ethylthymine, Is Dependent upon $O^6$-Alkylguanine-DNA Alkyltransferase and Nucleotide Excision Repair Activities in Human Cells" *Cancer Research*, Apr. 1, 1992, 52(7):2008-2011.

Engelbergs, J. et al. "Fast repair of $O^6$-ethylguanine, but not $O^6$-methylguanine, in transcribed genes prevents mutation of H-*ras* in rat mammary tumorigenesis induced by ethylnitrosourea in place of methylnitrosourea" *Proceedings of the National Academy of Sciences*, Feb. 17, 1998, 95(4):1635-1640.

Carmella, S.G. et al. "Ethylation and methylation of hemoglobin in smokers and non-smokers" *Carcinogenesis*, Nov. 2002, 23(11):1903-1910.

METHOD OF DETECTING ETHYLATED THYMIDINE DNA ADDUCTS

CROSS-REFERENCE TO RELATED APPLICATION

This application claims the benefit under 35 U.S.C. §119 of Taiwanese Patent Application No. 101116254, filed May 7, 2012, which is hereby incorporated by reference in its entirety.

BACKGROUND

1. Field of the Invention

The present invention relates to a method of analyzing DNA adducts, in particular to the method of analyzing ethylated thymidine DNA adducts.

2. Description of the Related Art

Humans are often exposed to various chemicals that will change the structure of DNA to produce excessive DNA adducts, and if these DNA adducts cannot be repaired effectively, mutation or carcinogenesis may occur. The amount of DNA adducts in tissues may reflect a balance between the capability of forming and the capability of repairing the adducts in the tissues when the tissues is chemically damaged. Since DNA adducts participate in carcinogenesis, DNA adducts have been used as a biomarker of carcinogens and cancer risk assessments [1].

Alkylating agents are usually found in our living environment. For example, the smoke of cigarettes contains polycyclic aromatic hydrocarbons (PAHs) and tobacco related nitrosamines become potential alkylating agents after a metabolism takes place by cytochrome P450 enzymes [2, 3]. A direct reaction of non-bulky alkylating agents usually occurs in the smoke of cigarettes. Methylated and ethylated DNA adducts were found in human tissues and urine [4-13]. Unlike the methylated DNA adducts, some researches discovered that the amount of ethylated DNA adducts in smokers is higher than that in nonsmokers [5, 6, 9-13]. The ethylation of DNA may occur on phosphate backbone [14, 15] or on bases of DNA. For example, reports [8-13, 16] show that ethylations are found at positions such as $N^3$ of adenine, $O^6$ and $N^7$ of guanine, and $O^2$, $O^4$, and $N^3$ of thymidine (as shown in FIG. 1). In an ethylated DNA adduct, $O^6$-ethylguanine ($O^6$-edT) and $O^4$-ethylthymidine ($O^4$-edT) will cause miscoding lesions, and researches of animal models discovered that these adducts are related to carcinogenesis [17, 18]. In addition, $O^6$-ethylguanine can be repaired effectively, but $O^2$-ethylthymidine ($O^2$-edT) or $O^4$-ethylthymidine ($O^4$-edT) cannot be repaired effectively [18-22]. Both $O^2$-edT and $O^4$-edT are accumulated in living organisms to cause persistent DNA lesions [18-20]. 3-ethyladenine and $N^7$-ethylguanine can be spontaneous depurinated and can be detected in a smoker's urine [9-11].

In smokers' urine, the average amount of 3-ethyladenine is higher than that of non-smokers [9, 10]. Similarly, the average amount of $N^7$-ethylguanine in smokers' urine and liver is higher than that of non-smokers [11, 12]. The amount of $O^4$-edT in the DNA of cancer patients' lung is directly proportional to the amount of PAH-DNA adducts, showing that these two DNA adducts are formed mainly by the smoke of cigarettes as an exposure source [5]. Further, some researches pointed out that the average amount of N-ethylvaline in smokers' hemoglobin rises significantly than that of non-smokers [23]. From the aforementioned results, we can derive that these ethylated DNA adducts may be produced by the ethylating agents in the smoke of cigarettes.

In an evaluation of the role of the ethylated DNA adducts played in the carcinogenesis, a highly sensitive, specific, qualitative and quantitative method is required to analyze the ethylated DNA adducts in vivo. Gas chromatography with electron impact ionization mass spectrometry (GC-EI/MS) was used by previous studies to analyze 3-ethyladenine in urine [8-10]. However, liquid chromatography together with electrospray ionization tandem mass spectrometry (LC-ESI/MS/MS) was used for the analysis of $N^7$-ethylguanine in human urine and liver samples [11, 12].

In a complicated matrix, an appropriate internal standard is generally required for quantifying a trace of analyte accurately. However, an isotopomer with the same structure of the analyte has the same expected physical and chemical properties of the analyte except in the mass spectrometer, so that the isotopomer can be used as an ideal internal standard. The stable isotope-labeled internal standard also can be used as a carrier for carrying a trace of analyte processed with a sample processing procedure. The isotope-labeled standard also can be used to label a signal position of the analyte in a chromatogram and used to find a peak of the analyte from the standard in the complicated chromatogram via the isotope according to the substantially the same retention time.

Up to now, there is no method primarily using the mass spectrometer to analyze ethylated thymidine DNA adducts. Present researches have succeeded detecting and quantifying $O^4$-edT, which induces mutation, in healthy persons' livers [4], cancer patents' lung tissues [5], cells of lower respiratory tracts [6], and smokers' lung tissues [13]. However, the white blood cells of healthy ones have not been used for the detection of $O^4$-edT. In these researches, the detection of $O^4$-edT adopts the $^{32}$P-postlabeling technique. Unlike the stable isotope dilution chromatography, internal standards [5, 6, 13] used in the $^{32}$P-postlabeling technique have different structures and retention time for the high-performance liquid chromatography (HPLC) and thin layer chromatography (TLC) are different from those of the analytes.

In summation, the conventional methods for detecting DNA adducts require a large number of samples, fail to find the distributed positions of the analytes from the chromatogram easily, and fail to detect several adducts at the same time, thus the conventional methods have the drawbacks of wasting labor, materials and examination time, and also have the shortcoming of a low sensitivity. Therefore, the inventor of the present invention designs a method of analyzing ethylated thymidine DNA adducts to overcome the drawbacks of the prior art and enhanced industrial applications.

References (1) Vineis, P.; Perera, F. *Int. J. Cancer* 2000, 88, 325-328.
(2) Thompson, C. L.; McCoy, Z.; Lambert, J. M.; Andries, M. J.; Lucier, G. W. *Cancer Res.* 1989, 49, 6503-6511.
(3) Hecht, S. S. *Mutat. Res.* 1999, 424, 127-142.
(4) Kang, H. O.; Konishi, C.; Kuroki, T.; Huh, N. H. *Carcinogenesis* 1995, 16, 1277-1280.
(5) Godschalk, R.; Nair, J; Schouten, F. J.; Risch, A.; Drings, P.; Kayser, K.; Dienenann, H.; Bartsch, H. *Carcinogenesis* 2002, 23, 2081-2086.
(6) Godschalk, R.; Nair, J; Kliem, H. C.; Wiessler, M.; Bouvier, G.; Bartsch, H. *Chem. Res. Toxicol.* 2002, 15, 433-437.
(7) Eberle, G.; Glüsenkamp, K.; Drosdziok, W.; Rajewsky, M. F. *Carcinogenesis* 1990, 11, 1753-1759.
(8) Prevost, V.; Shuker, D. E.; Friesen, M. D.; Eberle, G.; Rajewsky, M. F.; Bartsch, H. *Carcinogenesis* 1993, 14, 199-204.

(9) Kopplin, A.; Eberle-Adamkiewicz, G.; Glusenkmo, K. H.; Nehls, P.; Kirstein, U. *Carcinogenesis* 1995, 16, 2637-2641.
(10) Prevost, V.; Shuker, D.; E. *Chem. Res. Toxicol.* 1996, 9, 439-444.
(11) Chao, M.-R.; Wang, C.-J.; Chang, L. W.; Hu, C.-W. *Carcinogenesis* 2006, 27, 146-151.
(12) Chen, L. Wang, M. Villalta, P. W.; Hecht, S. S. *Chem. Res. Toxicol.* 2007, 20, 1498-1502.
(13) Anna, L.; Kovács, K.; Györffv, E.; Schoket, B.; Nair, J. *Mutagenesis* 2011, 26, 573-527.
(14) Singh, R.; Sweetman, G. M. A.; Farmer, P. B.; Shuker, D. E. G.; Rich, K. *J. Chem. Res. Toxicol.* 1997, 10, 70-77.
(15) Haglund, J.; Van Dongen, W.; Lemiere, F.; Esmans, E. L. *J. Am. Soc. Mass Spectrom.* 2004, 15, 593-606.
(16) Swann, P. F. *Mutat. Res.* 1990, 233, 81-94.
(17) Swenberg, J. A.; Dyroff, M. C.; Bedell, M. A.; Popp, J. A.; Huh, N.; Kirstein, U.; Rajewsky, M. F. *Proc. Natl. Acad. Sci. U.S.A.* 1984, 81, 1692-1695.
(18) Scherer, E.; Timmer, A. P.; Emmelot, P. *Cancer Lett.* 1980, 10, 1-6.
(19) Den Engelse, L.; De Graaf, A.; De Brij, R. J.; Menkveld, G. J. *Carcinogenesis* 1987, 8, 751-757.
(20) Thomale, J.; Huh, N. H.; Nehls, P.; Eberle, G.; Rajewsky, M. F. *Proc. Natl. Acad. Sci. U.S.A.* 1990, 87, 9883-9887.
(21) Bronstein, S. M.; Skopek, T. R.; Swenberg, J. A. *Cancer Res.* 1992, 52, 2008-2011.
(22) Engelberg, J.; Thomale, J.; Galhoff, A.; Rajewsky, M. F. *Proc. Natl. Acad. Sci. U.S.A.* 1998, 95, 1635-1640.
(23) Cannella, S. G.; Chen, M.; Villalta, P. W.; Gurney, J. G.; Hatsukami, D. K.; Hecht, S. S. *Carcinogenesis* 2002, 23, 1903-1910.

BRIEF SUMMARY

In view of the shortcomings of the prior art, it is a primary objective of the present invention to provide a method of analyzing ethylated thymidine DNA adducts to overcome the shortcomings of the conventional detection methods that require a large amount of samples, fail to find the distribution of the analytes in the chromatogram easily, and fail to detect several adducts at the same time, thus the conventional methods have the drawbacks of wasting labor, materials and examination time, and also have the shortcoming of a low sensitivity. Another objective of the present invention is to provide a method of analyzing ethylated thymidine DNA adducts, comprising the steps of: providing a leukocyte DNA; adding at least one isotope-labeled internal standard and a plurality of enzymes into the leukocyte DNA to hydrolyze the leukocyte DNA into a plurality of nucleosides; using a solid-phase extraction column to extract the plurality of adducted nucleosides; and using an isotope dilution nanoflow liquid chromatography-nanospray ionization tandem mass spectrometry (nanoflow LC-NSI/MS/MS) to detect and quantify at least one ethylated thymidine DNA adduct in the plurality of extracted nucleoside.

Preferably, the at least one ethylated thymidine DNA adduct may comprise $O^2$-ethylthymidine ($O^2$-edT), $N^3$-ethylthymidine ($N^3$-edT) and $O^4$-ethylthymidine ($O^4$-edT).

Preferably, detection limits of $O^2$-ethylthymidine, $N^3$-ethylthymidine and $O^4$-ethylthymidine may be equal to 5.0 fg, 10 fg and 10 fg, respectively.

Preferably, quantification limits of $O^2$-ethylthymidine, $N^3$-ethylthymidine and $O^4$-ethylthymidine may be equal to 50 fg, 100 fg and 100 fg, respectively.

Preferably, the at least one isotope-labeled internal standard may comprise $[^{13}C_{10},^{15}N_2]O^2$-edT, $[^{13}C_{10},^{15}N_2]N^3$-edT and $[^{13}C_{10},^{15}N_2]O^4$-edT.

Preferably, the plurality of enzyme comprises DNase 1, phosphodiesterase I, and alkaline phosphatase.

Preferably, an amount of the leukocyte DNA may be at least 50 μg.

Preferably, the isotope dilution nanoflow liquid chromatography-nanospray ionization tandem mass spectrometry has a spray voltage ranging from 1.3 kV to 2.0 kV.

Preferably, the isotope dilution nanoflow liquid chromatography-nanospray ionization tandem mass spectrometry has a source temperature from 200° C. to 300° C.

Preferably, the isotope dilution nanoflow liquid chromatography-nanospray ionization tandem mass spectrometry further has a collision energy from 5 V to 40 V.

Preferably, the isotope dilution nanoflow liquid chromatography-nanospray ionization tandem mass spectrometry has an analysis mode being a highly selective reaction monitoring (H-SRM) mode.

In summation, the method for analyzing ethylated thymidine DNA adducts in blood in accordance with the present invention has one or more of the following advantages:

(1) The analysis method of the present invention obtains a sample by a less intrusive method, so that the sample can be obtained easily.

(2) The analysis method of the present invention can detect several ethylated thymidine DNA adducts at the same time to reduce the examination time, the manpower for the operation, and the waste of materials.

(3) The analysis method of the present invention is highly sensitive, and just requires a small amount of sample to complete the analysis.

DETAILED DESCRIPTION

Figure 1:
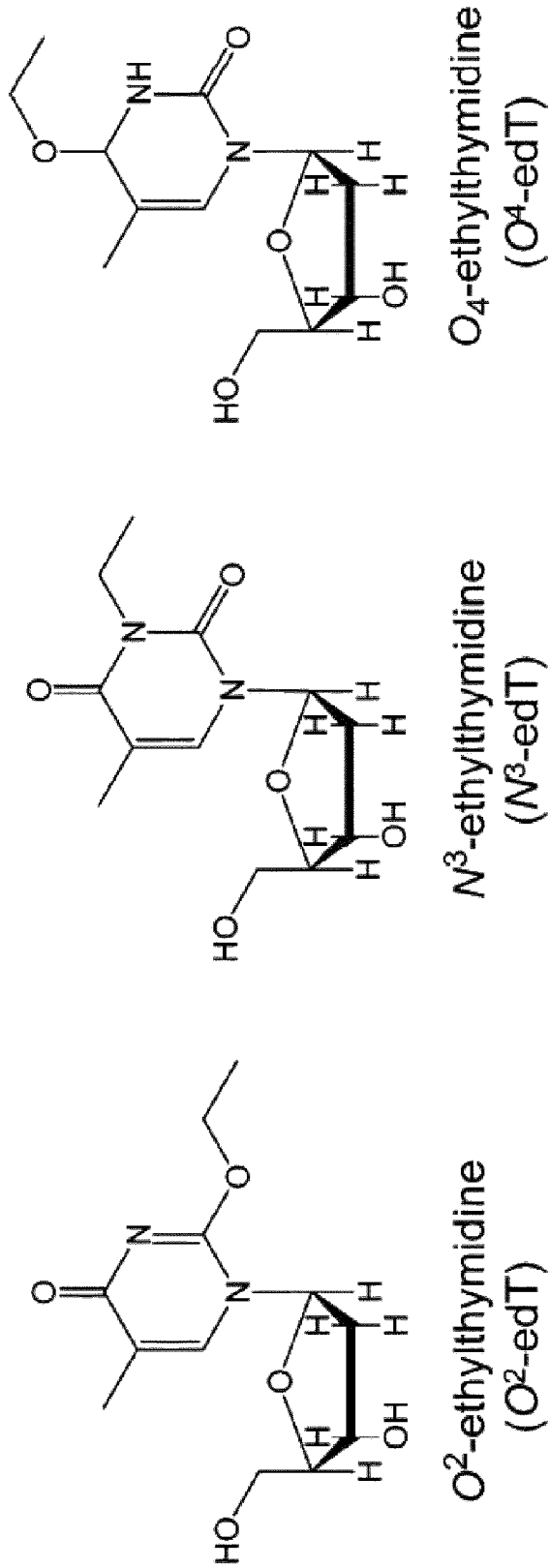
FIG. 1 is a schematic view of structures of ethylated thymidine DNA adducts analyzed by an analysis method of the present invention.

The technical characteristics of the present invention will become apparent with the detailed description of the preferred embodiments accompanied with the illustration of related drawings as follows. It is noteworthy that same numerals are used for representing the same respective elements in the drawings, and the drawings are provided for the purpose of illustrating the invention, but not intended for limiting the scope of the invention.

The method for analyzing ethylated thymidine DNA adducts of the present invention is a highly sensitive quantification method that uses leukocyte DNA as a sample, and a stable isotope dilution nanoflow liquid chromatography-nanospray ionization tandem mass spectrometry (nanoflow LC-NSI/MS/MS) is used to detect and quantify one or more ethylated thymidine DNA adducts in a highly selective reaction monitoring (H-SRM) mode, wherein the ethylated thymidine DNA adducts include $O^2$-edT, $N^3$-edT and $O^4$-edT. A preferred embodiment is used for illustrating the present invention as follows.

With reference to FIG. 1 for a schematic view of structures of ethylated thymidine DNA adducts detected by an analysis method of the present invention, the detected ethylated thymidine DNA adducts have an ethyl group added at $O^2$, $N^3$, and $O^4$ positions of thymidine.

Figure 2:
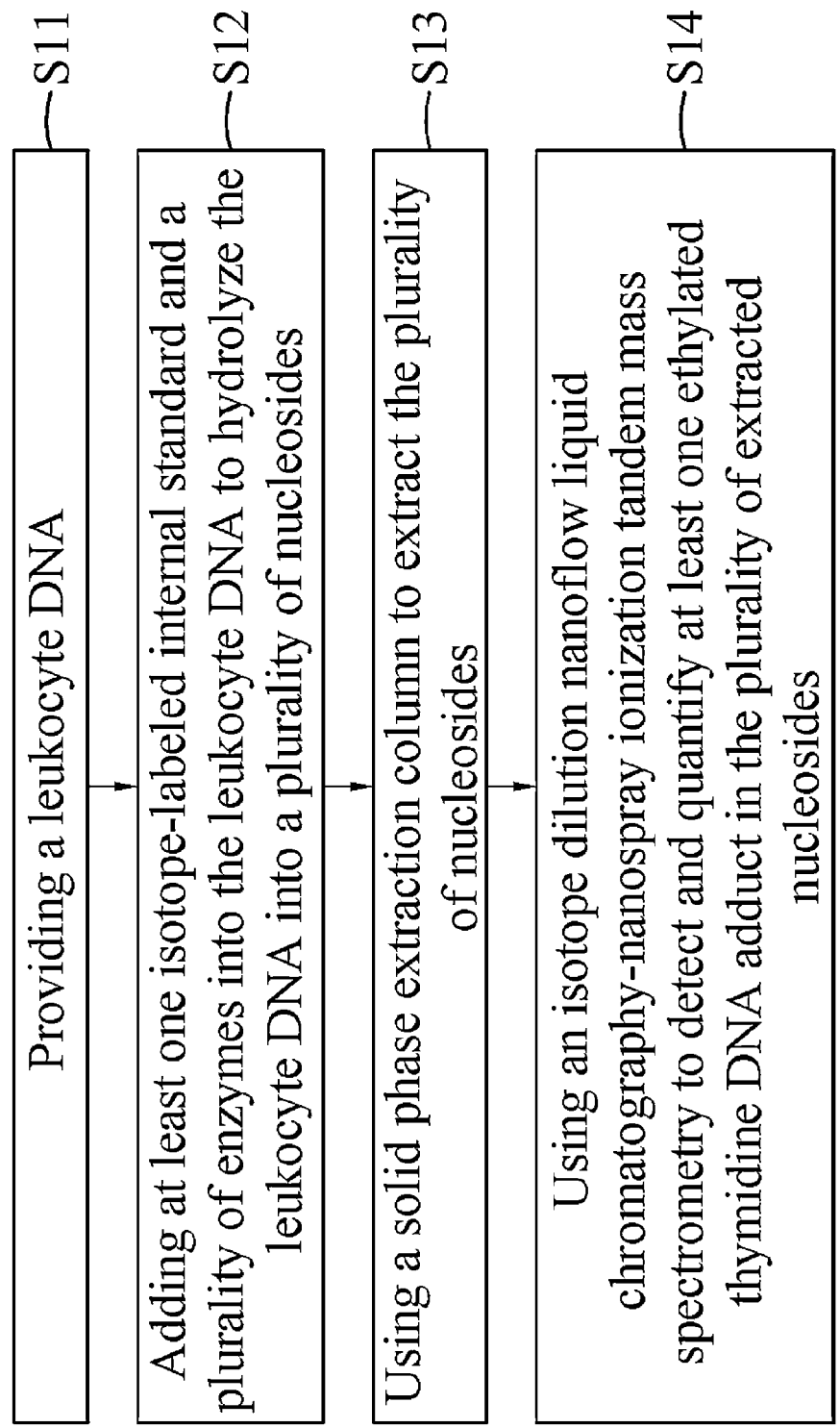
FIG. 2 is a flow chart of an analysis method in accordance with a preferred embodiment of the present invention.

With reference to FIG. 2 for a flow chart of a method of analyzing ethylated thymidine DNA adducts in accordance with a preferred embodiment of the present invention, the method comprises the following steps:

S11: Providing a leukocyte DNA.

S12: Adding at least one isotope-labeled internal standards and a plurality of enzymes into the leukocyte DNA to hydrolyze the leukocyte DNA into a plurality of nucleosides.

S13: Using a solid-phase extraction column to extract the plurality of adducted nucleosides.

S14: Using an isotope dilution nanoflow liquid chromatography-nanospray ionization tandem mass spectrometry (nanoflow LC-NSI/MS/MS) to detect and quantify at least one ethylated thymidine DNA adducts in the plurality of extracted nucleosides.

Experiment Method

HPLC-UV Experiment Conditions of High-performance Liquid Chromatography (HPLC)

A HPLC-UV system includes a photodiode array detector (L-7450A), a D-7000 interface (provided by Hitachi, Tokyo, Japan), a Rheodyne injector, and a reversed phase C18 column (provided by Gemini C18 (2), and a Hitachi L-7000 pump system of the dimensions 4.6 mm×250 mm, 5 μm, 100 Å, Phenomenex, Torrance, Calif.). From 0 to 30 minutes, an aqueous methanol with a linear concentration gradient from 0 to 100% is used for elution at a speed of 1.0 mL/min. Wherein, the concentration of the methanol is maintained at 100% for 10 minutes before deionized water (100%) is used for rinsing and balancing.

Nuclear Magnetic Resonance (NMR) Spectroscopy

A nuclear magnetic resonance (NMR) spectrometer (Varian-Unity INOVA-500 MHz NMR spectrometer) is used to record the NMR spectra of $^1H$ and $^{13}C$. The chemical migration uses tetramethylsilane as internal standard, which is expressed in terms of parts per million (ppm).

Synthesis of $O^2$-edT, $N^3$-edT and $O^4$-edT Standards

N-Ethyl-N-nitrosourea (150 mg, 1.28 mmol) is dissolved in 1.0 mL of potassium hydroxide solution (KOH, 40%) and 1.5 mL of diethyl ether, and stirred vigorously at 0° C. for 20 minutes to produce diazoethane. 2'-deoxythymidine (1.0 mg, 4.13 nmol) dissolved in 0.7 mL of methanol is added onto the top layer of the solution, and stirred at room temperature for 1 hour. The mixture is analyzed by HPLC-UV, and $O^2$-edT is collected from 15 to 16.5 minutes, $N^3$-edT is collected from 17 to 18.5 minutes, and $O^4$-edT is collected from 19 to 20.5 minutes, and all collections are dried.

Synthesis of $[^{13}C_{10},^{15}N_2]O^2$-edT, $[^{13}C_{10},^{15}N_2]N^3$-edT and $[^{13}C_{10},^{15}N_2]O^4$-edT Standards This procedure is the same as that of the synthesis of $O^2$-edT, $N^3$-edT and $O^4$-edT. The ESI-MS spectra of $[^{13}C_{10},^{15}N_2]O^2$-edT, $[^{13}C_{10},^{15}N_2]N^3$-edT and $[^{13}C_{10},^{15}N_2]O^4$-edT show a m/z 283 ($[M+H]^+$). The collision-induced dissociation mass spectra of $[^{13}C_{10},^{15}N_2]O^2$-edT, $[^{13}C_{10},^{15}N_2]N^3$-edT and $[^{13}C_{10},^{15}N_2]O^4$-edT show a m/z 162 ($[M+H-dR]^+$) at 10 eV and a m/z 134 ($[M+H-dR-C_2H_4]$) at 25 eV.

Extraction of DNA from Blood

10% (v/v) of citrate-dextrose solution (ACD) is used as an anticoagulant, and human blood is drawn and stored at 4° C. 1.1 mL of the blood/anticoagulant mixture is prepared, and a blood DNA extraction kit (Blood Genimic Midi kit, Viogen, Sunnyvale, Calif.) is operated to extract DNA of the blood according to the operating manual. A spectrophotometer (Implen, Inc. Westlake Village, Calif.) is used to quantify the blood DNA, and the purity of the blood DNA is examined by using the absorbance ratio ($A_{260}/A_{280}$) and the ratio must fall within the range from 1.8 to 2.0 before the following experiment is conducted.

Iodoethane-Treated Calf Thymus DNA

In the solution containing deionized water (583 μL) and calf thymus DNA (1.0 mg), N,N-dimethylformamide (DMF, 50 μL) containing iodoethane (20 μL, 0.25 mmol) is added, and the mixture is stirred vigorously at 58° C. for 12 hours, and then the pH value is adjusted to 7.0. The solution is extracted by using dichloromethane (10 mL) and hexane (10 mL) sequentially to remove the iodoethane from the solution.

Enzyme Hydrolysis DNA

In the above DNA solution, 100 pg each of $[^{13}C_{10},^{15}N_2]O^2$-edT, $[^{13}C_{10},^{15}N_2]N^3$-edT and $[^{13}C_{10},^{15}N_2]O^4$-edT are added to act as internal standards, and an enzyme hydrolysis is performed. The DNA (50 μg), internal standards, 10.2 units of DNase 1, 10 mM sodium citrate (pH 6.5), and 10 mM of magnesium chloride ($MgCl_2$) are mixed, and then set still at 37° C. for 1 hour. 0.0016 unit of phosphodiesterase 1 and 0.03 unit of alkaline phosphatase of the pre-mixed Tris buffer (pH 8.0) are added and set still at 37° C. for 18 hours.

Adducts Enrichment

In a preferred embodiment of the present invention, the hydrolysate is filtered by 0.22-μm nylon syringe filter and then by a solid-phase extraction column (SPE). After a Bond Elut Bonded phase C18-OH, nonend-capped, 500 mg, 3 mL, Varian; Harbor City, Calif.) is rinsed and balanced by 15 mL of methanol and water, the solid-phase extraction column is used to purify a DNA adduct existed in form of a plurality of nucleosides. And then, the solid-phase extraction column is washed by 12 mL of water and 3 mL of water solution (15%) containing methanol, and 3 mL of aqueous methanol (40%) is added to collect the hydrolysate. The hydrolysate is dried and dissolved in 10 μL of acetic acid (0.1%, pH 3.2), and then the 0.22-μm nylon syringe filter is used for the filter again. Finally, 2 μL of the processed sample is analyzed by the isotope dilution nanoflow liquid chromatography-nanospray ionization tandem mass spectrometry.

Nanoflow LC-NSI/MS/MS Analysis

In a preferred embodiment of the present invention, a 2-μL injection loop is connected to a 6-port switching valve of a liquid phase chromatography system, wherein the liquid phase chromatography system is comprised of a liquid phase chromatography system (UltiMate 3000 Nano LC system; Dionex, Amsterdam, Netherlands) and an internally filled reversed phase column (75 μm×11 cm, 5 μm; MAGIC C18AQ, 200 Å, 5 μm; Michrom BioResource, Auburn, Calif.). The pump out (30 μL/min) is divided in front of the injection loop into a flow of 300 nL/min. The mobile phase A is 0.1% of acetic acid (pH 3.2), and the mobile phase B is acetonitrile containing 0.1% of acetic acid. The elute falls within a range of 0 to 30 minutes, starting from a linear gradient from 10% of the mobile phase B to 100% of the mobile phase B, and then 100% of the mobile phase B is maintained for 10 minutes. The effluent is analyzed by a triple quadrupole mass spectrometer (TSQ Quantum Ultra EMR mass spectrometer; Thermo Electron Corp., San Jose, Calif.) having a nanospray ionization interface in a positive-ion mode of the nanospray ionization tandem mass spectrometer. The spray is monitored and controlled by a built-in charge coupling device (CCD) camera. The voltage of the spray falls within a range from 1.3 kV to 2.0 kV, preferably from 1.5 kV to 1.8 kV; and the source temperature falls within 200° C. to 300° C., preferably 230° C. to 270° C. Argon is used as a collision gas in the mass spectroscopy experiment, and the collision gas has pressure of 1.5 mTorr and collision energy of 5 V to 40 V, preferably 10 V to 30 V. In this preferred embodiment, the spray is conducted with a voltage of 1.5 kV, a source temperature of 270° C. and a collision energy of 10 V, and these experiment conditions are used as examples, but the invention is not limited to these conditions only.

The stable isotope dilution nanoflow liquid chromatography-nanospray ionization tandem mass spectrometry is used for analyzing the enriched adduct sample, and a highly selective reaction monitoring (H-SRM) mode is used for the analysis, wherein Q1 and Q3 have mass widths of m/z 0.2 and m/z 0.7 respectively, and the dwell time of 0.1 second. A first quadrupole (Q1) selects an ionized parent ion [M+H] and a collision takes place in a collision cell (Q2) to produce product ions, and specific daughter ions are selected in the third quadrupole (Q3) for further analyses. Two highly selective reaction monitoring methods are used here. In Method 1, a collision energy of 10V is applied to a position having a m/z 271.1 in Q1 to detect $O^2$-edT, $N^3$-edT and $O^4$-edT, and daughter ions [M+H-116] ([M+H-dR]$^+$) are detected at a position having a m/z 155.1 in Q3 and [$^{13}C_{10}$,$^{15}N_2$]$O^2$-edT, [$^{13}C_{10}$,$^{15}N_2$]$N^3$-edT and [$^{13}C_{10}$,$^{15}N_2$]$O^4$-edT are detected at positions having a m/z 283.1 in Q1 and m/z 162.1 in Q3 respectively by a collision energy of 10 V. In Method 2, $O^2$-edT, $N^3$-edT and $O^4$-edT are detected at a position having a m/z 271.125 in Q1 and daughter ions [M+H-144]$^+$ ([M+H-dR-$C_2H_4$]$^+$) at positions having a m/z 127.1 in Q3 by a collision energy of 25 V. [$^{13}C_{10}$,$^{15}N_2$]$O^2$-edT, [$^{13}C_{10}$,$^{15}N_2$]$N^3$-edT and [$^{13}C_{10}$,$^{15}N_2$]$O^4$-edT are detected at positions having a m/z 283.1 in Q1 and a m/z 134.1 of Q3 respectively by a collision energy of 25 V.

Calibration Curves

[$^{13}C_{10}$,$^{15}N_2$]$O^2$-edT, [$^{13}C_{10}$,$^{15}N_2$]$N^3$-edT and [$^{13}C_{10}$,$^{15}N_2$]$O^4$-edT of 100 pg each and solutions of $O^2$-edT, $N^3$-edT and $O^4$-edT with different quantities (0, 0.05, 0.1, 0.2, 0.5, 1.0, 10 and 50 pg) are prepared. Each sample is processed by the aforementioned solid-phase extraction column. The sample containing the aforementioned adducts is dried and dissolved in 10 μL of 0.1% of acetic acid (pH 3.2) again, and finally 2 μL of the processed sample is taken out and analyzed by the nanoflow liquid chromatography-nanospray ionization tandem mass spectrometry (nanoflow LC-NSI/MS/MS).

Object of the Study

The method for analyzing ethylated thymidine DNA adducts in accordance with the present invention aims healthy adults as the object of the study, and these healthy adults were selected from the students and staffs of National Chung Cheng University, including 20 male smokers and 20 non-smokers (including 14 males and 6 females). The smokers have an average age of 21.9±5.2 (mean±SD), and the non-smokers have an average age of 25.3±6.5.

Statistical Analysis

GraphPad InStat version 3.00 (GraphPad Software, San Diego, Calif.) is used for the following statistical analysis, and a nonparametric Mann-Whitney test is used for analyzing the difference of $O^2$-edT, $N^3$-edT and $O^4$-edT in human leukocyte DNA samples of 20 smokers and 20 non-smokers, and the relation between each ethylated thymidine DNA adduct of a smoker and the smoking index (which is the number of cigarette per day×years of smoking) is analyzed. The correlation coefficient of any two adducts of the 40 samples are calculated by linear correlation.

Results and Discussion

Synthesis and Characterization of Standards

Figure 3A:
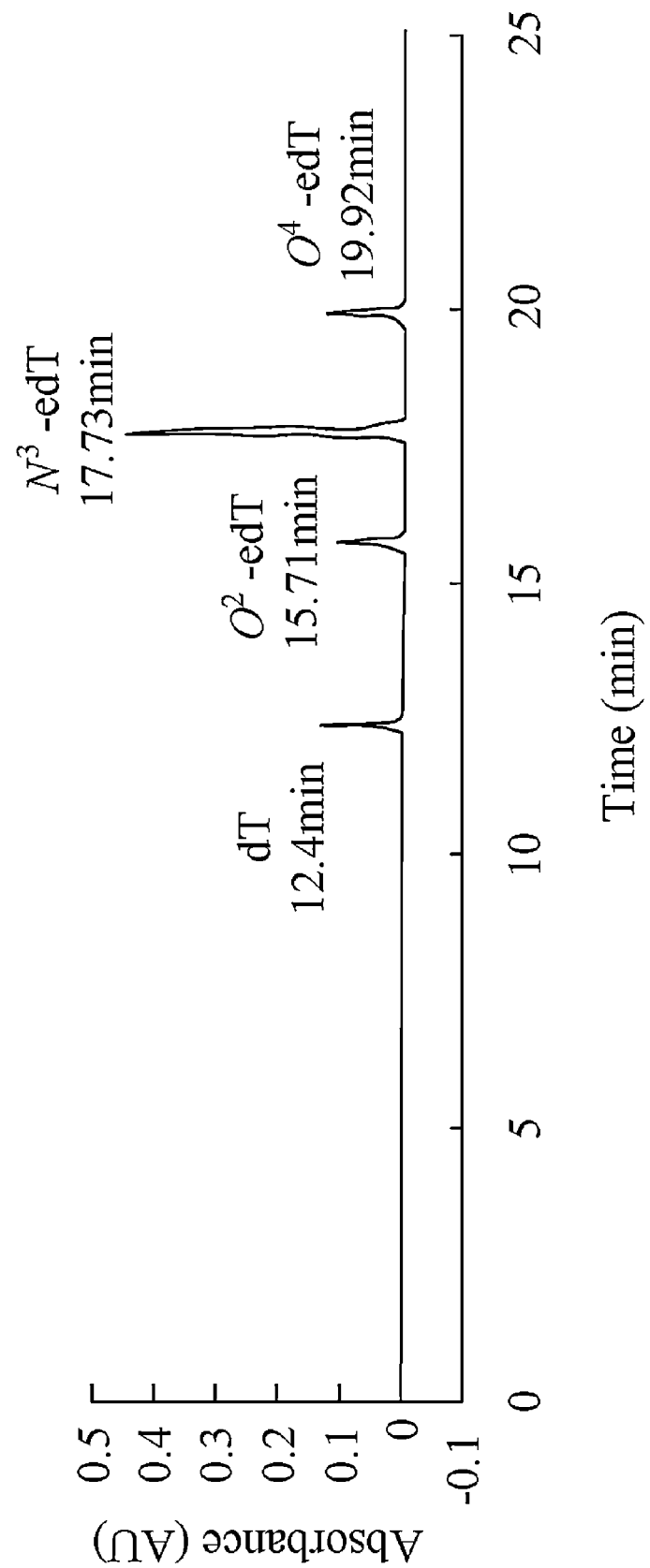
FIGS. 3A to 3D for chromatograms of ethylated thymidine DNA adducts analyzed by using HPLC in accordance with a preferred embodiment of the present invention, respectively.
Figure 3B:
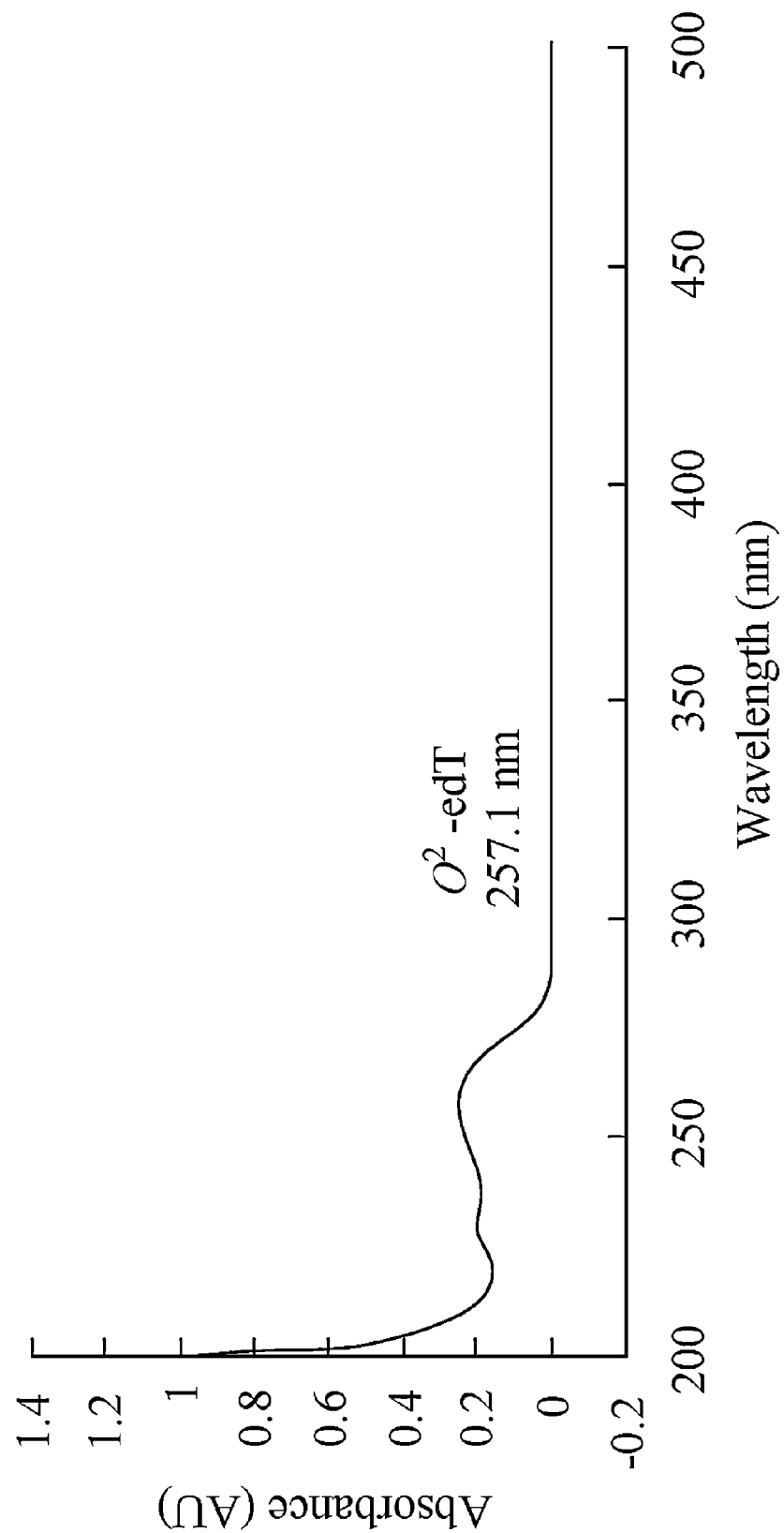
Figure 3C:
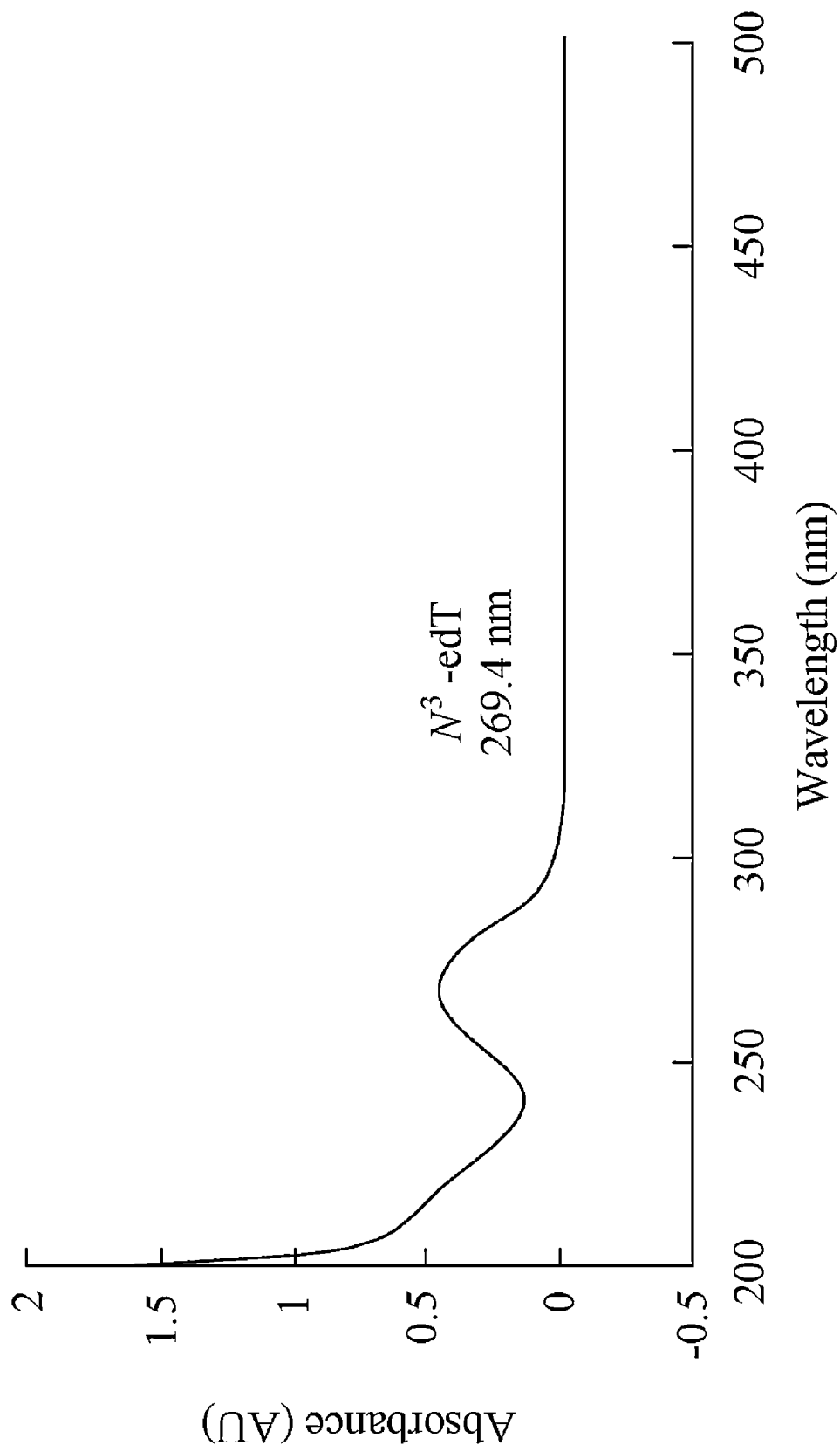
Figure 3D:
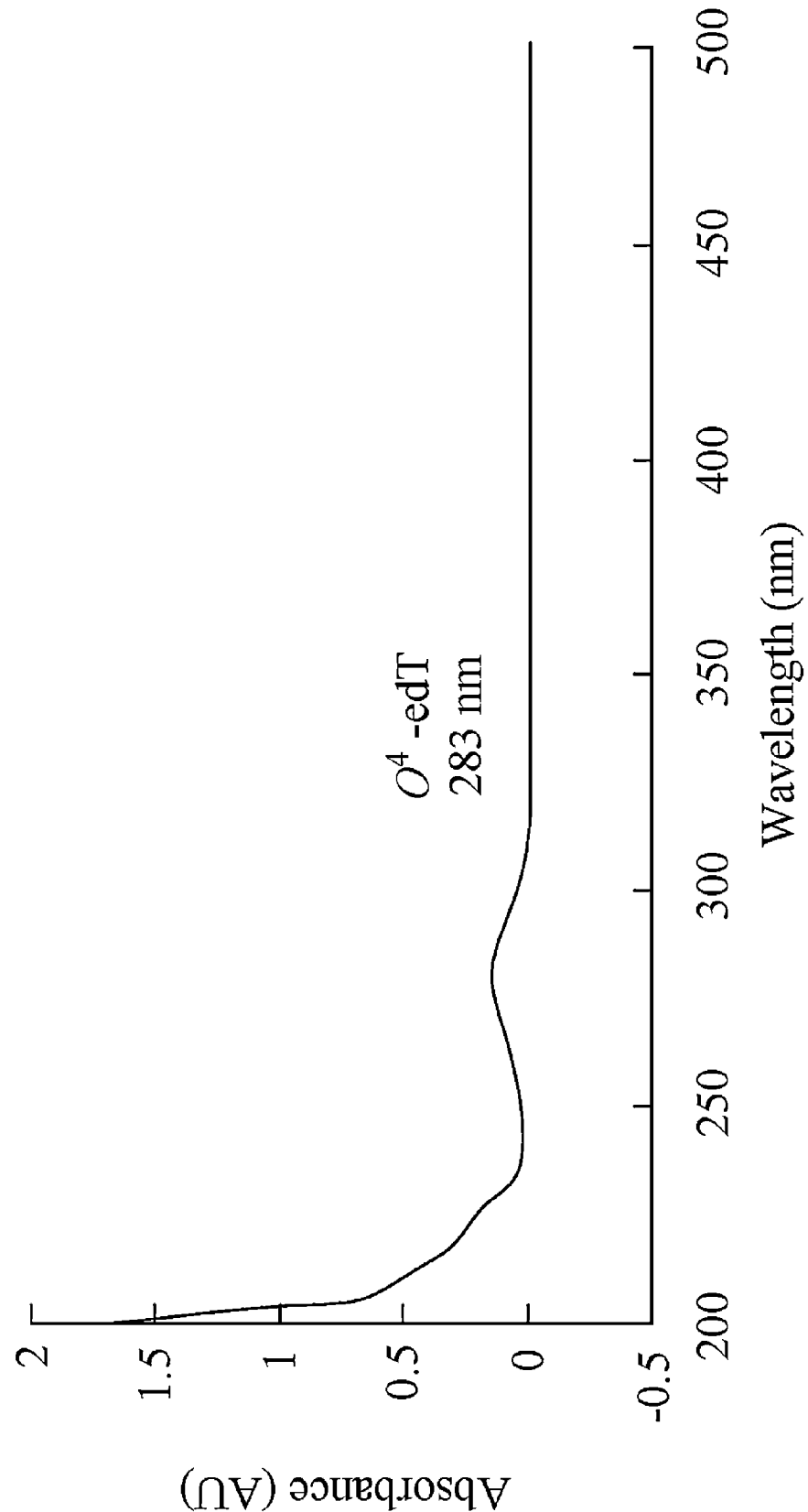

Standard $O^2$-edT, $N^3$-edT and $O^4$-edT are formed by a reaction of 2'-deoxythymidine with diazoethane. Wherein, the diazoethane can be synthesized by a reaction of N-ethyl-N-nitrosourea in an alkaline environment. With reference to FIGS. 3A to 3D for chromatograms of ethylated thymidine DNA adducts analyzed by using HPLC in accordance with a preferred embodiment of the present invention respectively, the three kinds of detected ethylated regioisomers have significantly different UV spectra (as shown in FIGS. 3B to 3D) and retention time (as shown in FIG. 3A).

Method Development

With reference to FIG. 2 for a flow chart of a method for analyzing ethylated thymidine DNA adducts in accordance with a preferred embodiment of the present invention, the method comprises the steps of: (1) adding internal standards [$^{13}C_{10}$,$^{15}N_2$]$O^2$-edT, [$^{13}C_{10}$,$^{15}N_2$]$N^3$-edT and [$^{13}C_{10}$,$^{15}N_2$]$O^4$-edT to DNA; (2) performing an enzyme hydrolysis; (3) using a reverse phase solid-phase extraction column to concentrate a DNA adduct; and (4) using a nanoflow liquid chromatography-nanospray ionization tandem mass spectrometry (nanoflow LC-NSI/MS/MS) for an analysis in a highly selective reaction monitoring (H-SRM) mode.

Method Performance and Validation

The highly sensitive nanoflow liquid phase chromatography system of the present invention is coupled to a triple quadrupole mass spectrometer for performing a monitoring in the highly selective reaction monitoring mode, wherein the first quadrupole and the third quadrupole are in a static mode for monitoring parent ions and daughter ions with specific m/z values. Since the nanoflow liquid chromatography-nanospray ionization tandem mass spectrometry (nanoflow LC-NSI/MS/MS) has a high sensitivity, therefore a small amount of adducts is formed during the quantification of the DNA sample, so as to reduce the required amount of the DNA sample. The combination of the nanoflow liquid phase chromatography system and the nanospray ionization tandem mass spectrometry (nanoflow LC-NSI/MS/MS) constitutes the most sensitive equipment. To improve the specificity of the analysis method of the present invention, the highly selective reaction monitoring mode with a narrower monitoring view (0.2 Da) is used for monitoring parent ions. Therefore, lesser ions are allowed to pass through the first quadrupole to reduce the background, and such method is especially applicable for analyzing complicated mixtures. In the analysis method of the present invention, the accuracy, precision and reproducibility of the analysis method are monitored and controlled by adding an isotopomer of the object to be tested into the sample at the beginning of the experiment as an internal standard. The present invention makes use of a conversion between two highly selective reaction monitoring modes for the monitoring. In other words, the third quadrupole monitors and detects the parent ion [M+H]$^+$ (m/z 271.1)

to be converted into the daughter ion $[M+H-116]^+$ ($[M+H-dR]^+$) (m/z 155.1, method 1); and converted into the daughter ion $[M+H-144]^+$ ($[M+H-dR-C_2H_4]^+$) (m/z 127.1, method 2). Since the signal intensity of the adduct obtained by Method 1 is equal to three times of the signal intensity of the adduct obtained by Method 2, the present invention can use Method 1 to quantify the ethylated thymidine DNA adduct.

The detection limit of $O^2$-edT, $N^3$-edT and $O^4$-edT by an on-column injection are 5.0 fg (18.5 amol), 10 fg (37 amol), and 10 fg (37 amol) respectively. By mixing 100 pg of [$^{13}C_{10}$, $^{15}N_2$]$O^2$-edT, [$^{13}C_{10}$,$^{15}N_2$]$N^3$-edT and [$^{13}C_{10}$,$^{15}N_2$]$O^4$-edT each, and adding different amounts of $O^2$-edT, $N^3$-edT and $O^4$-edT adduct standards, the steps of a solid phase extraction are carried out, and the nanoflow liquid chromatography-nanospray ionization tandem mass spectrometry is used to obtain the calibration curve. In a preferred embodiment, the quantification limit of the analysis method of the present invention use is defined as the minimum amount of the object to be tested in a linear calibration curve, wherein the quantification limits of $O^2$-edT, $N^3$-edT and $O^4$-edT are 50, 100 and 100 fg respectively. In other words, 1.2, 2.3 and 2.3 units of $O^2$-edT, $N^3$-edT and $O^4$-edT can be detected in every $10^9$ (50 μg) normal nucleosides. It shows that if 25 to 35 μg of DNA are extracted from every mL of blood, it requires 1.5 to 2 mL of blood for the experiment. Since the nanoflow liquid phase chromatography system can inject a maximum volume of 2 μL, therefore 10 μL of solvent is added and to dissolve the concentrated sample. Since only one-fifth of the concentrated sample is dissolved back to the nanoflow liquid chromatography-nanospray ionization tandem mass spectrometry for analysis, therefore the quantification limit of the analysis method of the present invention is at least five times of the detection limit of the on-column injection.

Figure 4A:
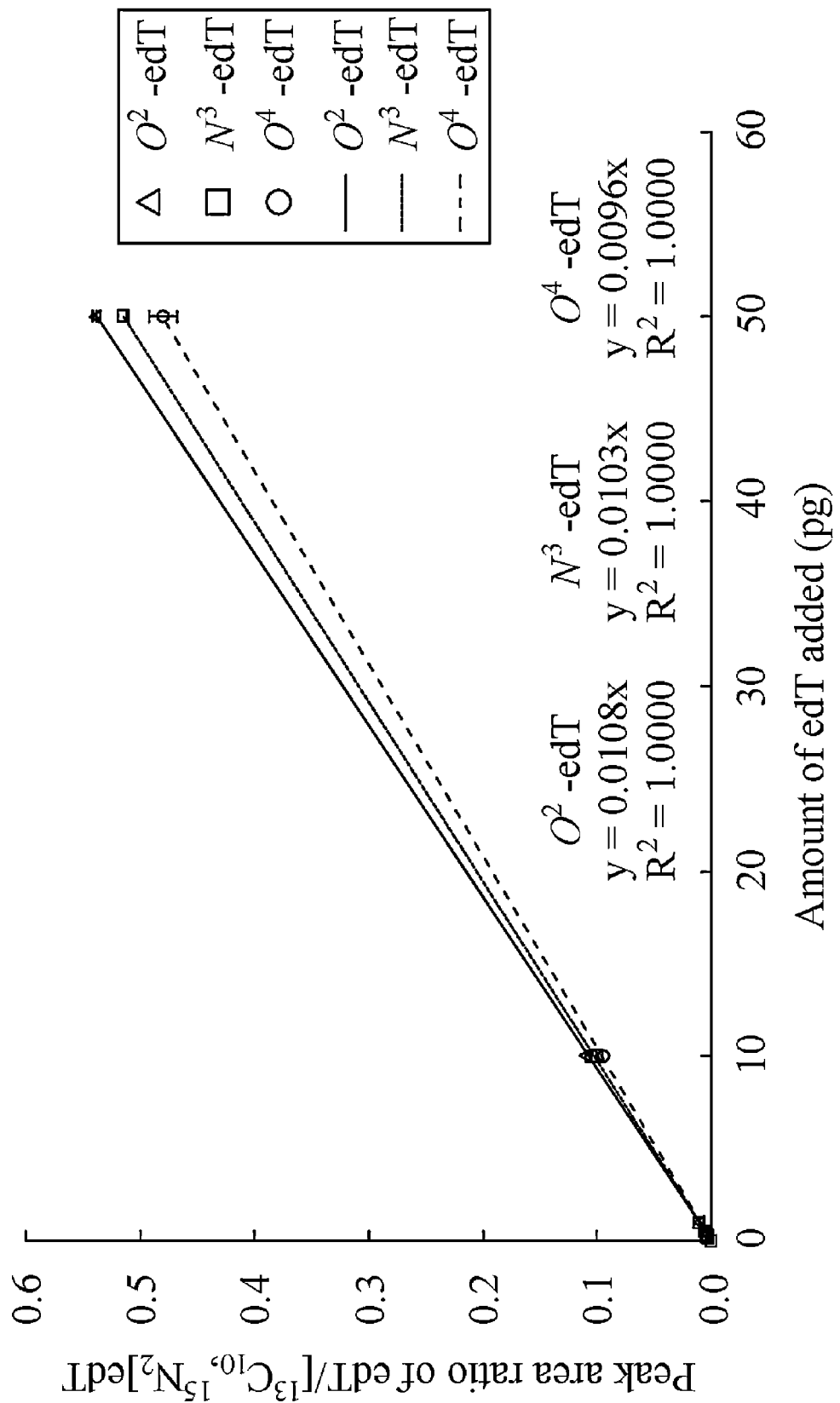
FIGS. 4A and 4B are calibration curves of quantified ethylated thymidine DNA adducts in accordance with a preferred embodiment of the present invention, respectively.
Figure 4B:
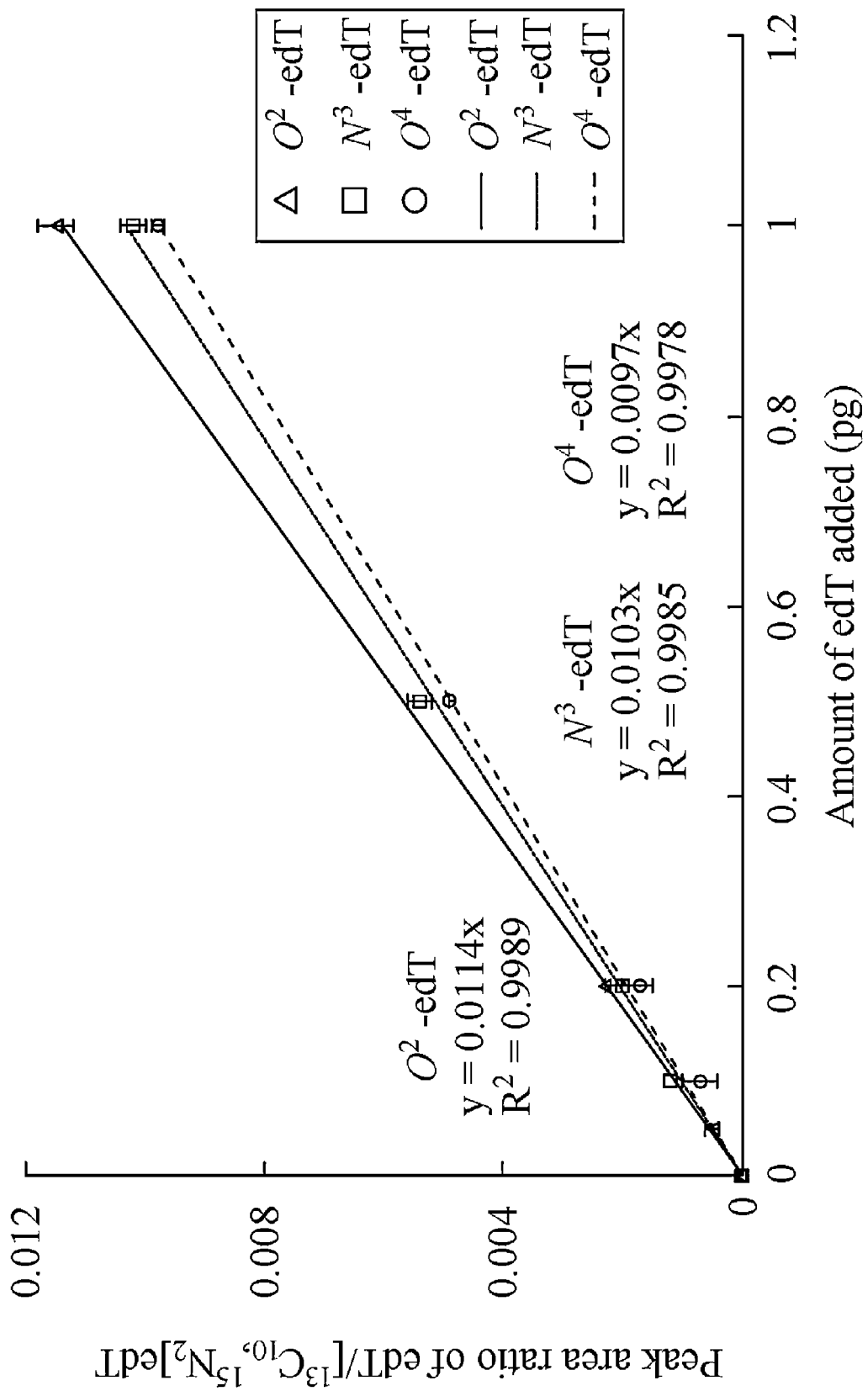

With reference to FIGS. 4A and 4B for calibration curves of quantified ethylated thymidine DNA adducts in accordance with a preferred embodiment of the present invention respectively, the calibration curves have good linearity, so that when the three kinds of DNA adducts are measured, the correlation coefficient (R2) is equal to 1.0000 within the detection range from the quantification limit to 50 pg as shown in FIG. 4A). With the detection range from the quantification limit to 1.0 pg, the correlation coefficients of $O^2$-edT, $N^3$-edT and $O^4$-edT are 0.9989, 0.9985, and 0.9978 respectively (as shown in FIG. 4B). In addition, if the sample only contains isotopes, the DNA adduct will not be detected, so that the calibration curve passes through the origin.

Figure 5A:
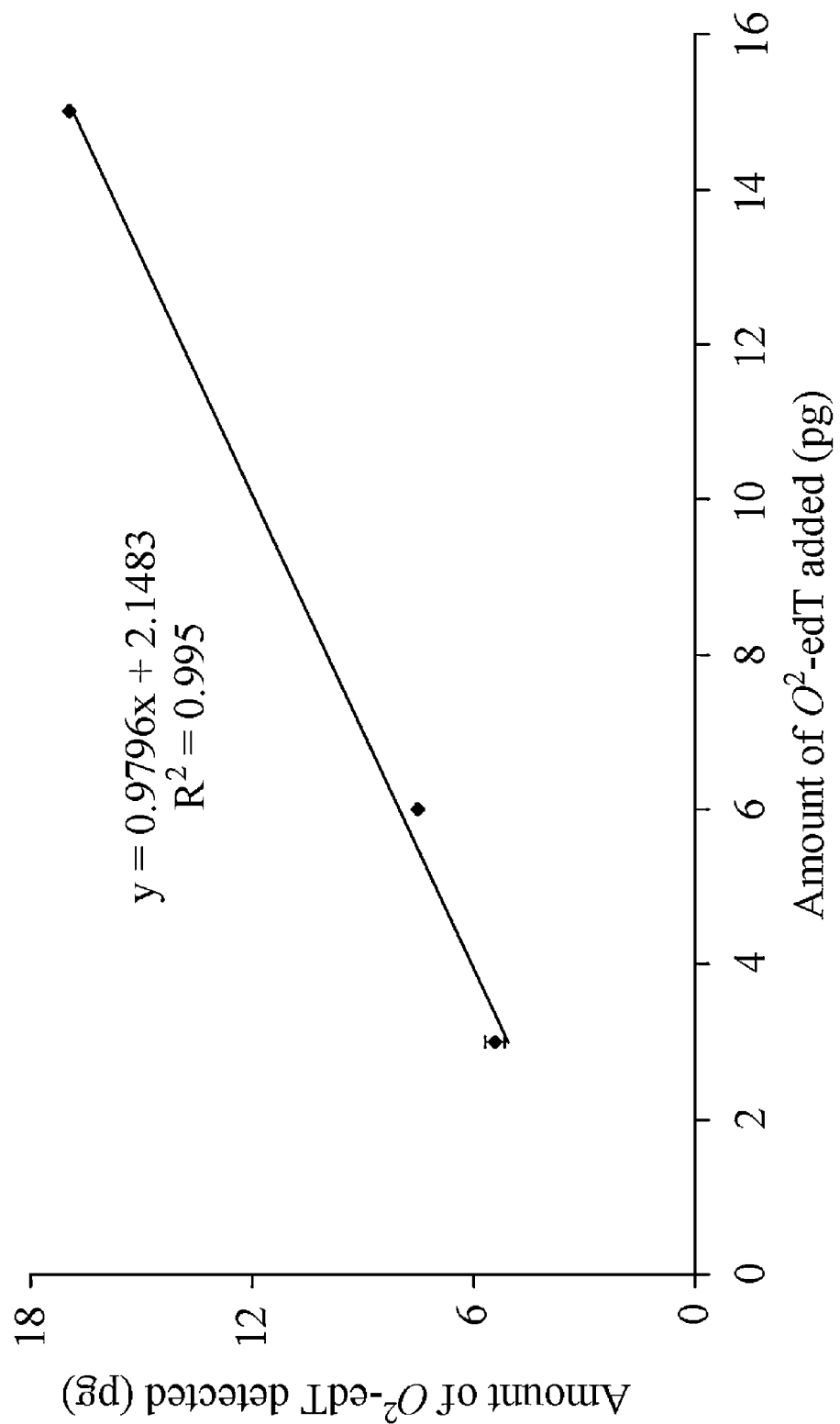
FIGS. 5A to 5C are schematic views of the accuracy of quantified ethylated thymidine DNA adducts in accordance with a preferred embodiment of the present invention, respectively.
Figure 5B:
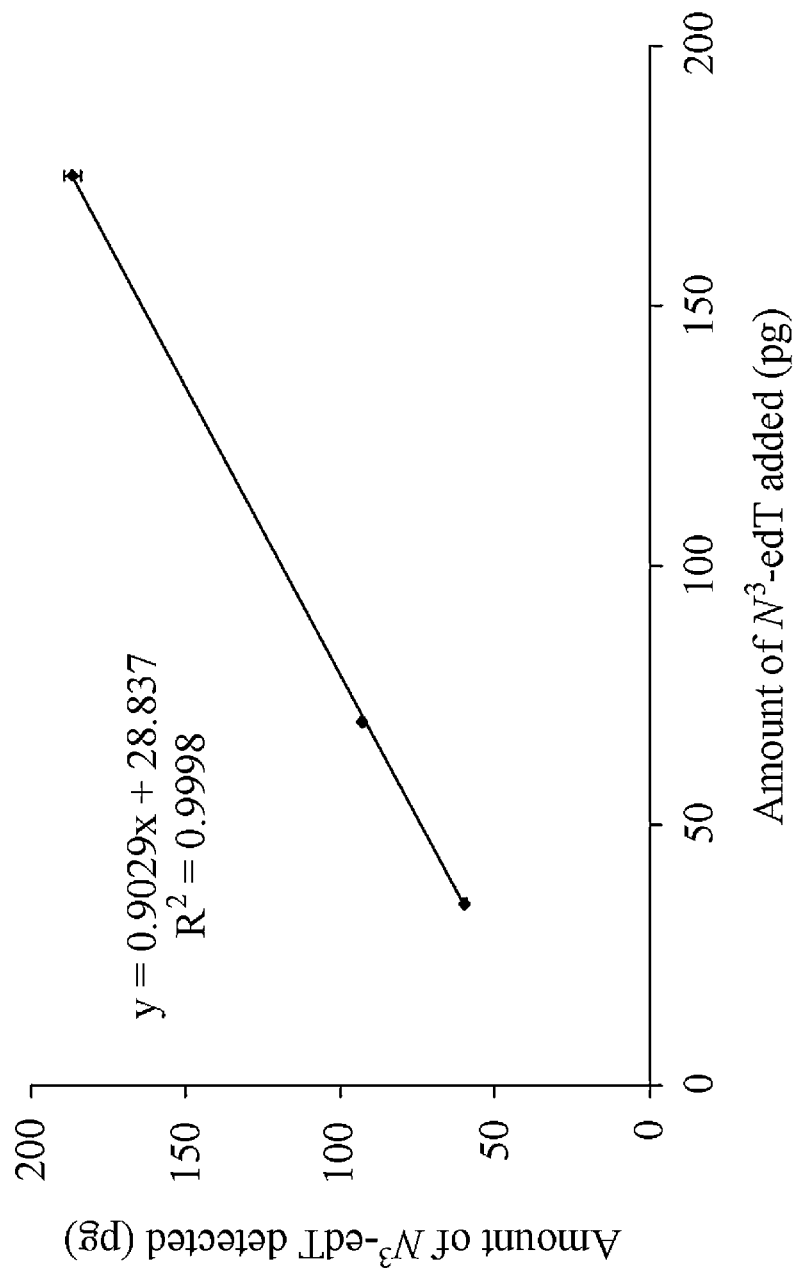
Figure 5C:
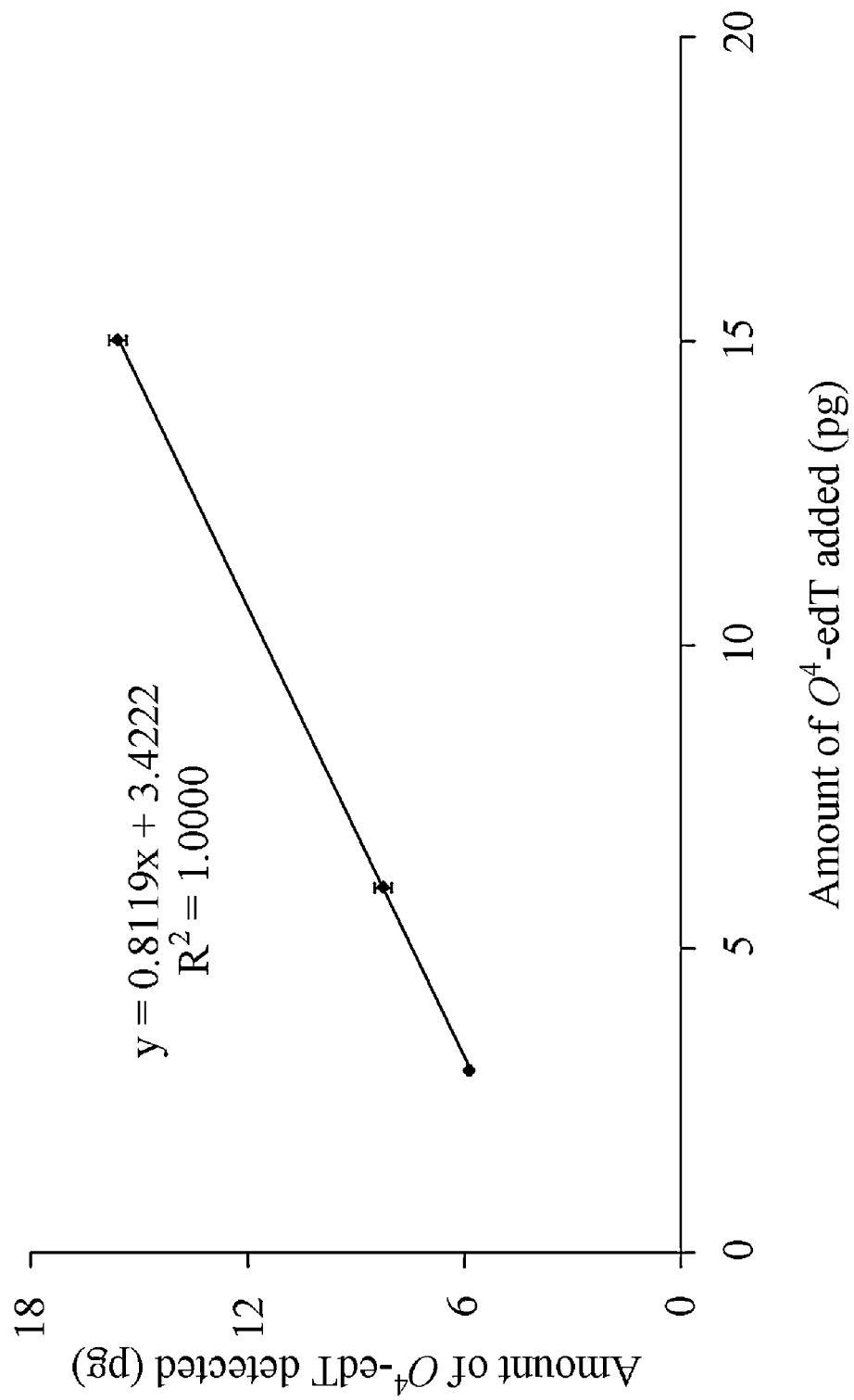

With reference to FIGS. 5A to 5C for schematic views of the accuracy of quantified ethylated thymidine DNA adducts in accordance with a preferred embodiment of the present invention respectively, a known amount of $O^2$-edT (3.0, 6.0, and 15 pg, as shown in FIG. 5A), $N^3$-edT (35, 70, and 175 pg, as shown in FIG. 5B) and $O^4$-edT (3.0, 6.0, and 15 pg, as shown in FIG. 5C) is added calf thymus DNA (10 μg) processed by iodoethane and unprocessed calf thymus DNA (40 μg) for the analysis to verify the accuracy of the analysis method of the present invention. In the figures, linear regression is used to obtain the y-intercepts of $O^2$-edT, $N^3$-edT and $O^4$-edT which are equal to 2.15, 28.84, and 3.42 pg, respectively, and have a high correlation coefficient. These amount are very close to the concentration of 2.22, 29.9, and 3.27 pg of $O^2$-edT, $N^3$-edT and $O^4$-edT detected in calf thymus DNA processed by iodoethane without adding 50 μg of the standards. In other words, 5.2, 70.5, and 7.7 units of DNA adducts are detected in every $10^8$ normal nucleosides.

The $O^2$-edT, $N^3$-edT and $O^4$-edT in the calf thymus DNA (5 times dilution, a total weight of 50 μg) processed by iodoethane are analyzed repeatedly, and the analysis is performed by the optimal experiment procedure continuously for three days to evaluate the precision of the analysis method of the present invention. Table 1 shows that the standard deviation falls within a range of 10% regardless of the analysis is repeated intraday or interday, and this result indicates that the analysis method of the present invention has a high reproducibility.

TABLE 1

| | Average Adducts Level (Adduct/$10^8$ nucleosides) ± Standard Deviation (Relative Standard Deviation, %) | | | |
|---|---|---|---|---|
| | First Day | Second Day | Third Day | Daytime Variation |
| $O^2$-edT | 5.7 ± 0.5 (9.16%) | 6.0 ± 0.2 (2.8%) | 5.2 ± 0.2 (4.0%) | 5.6 ± 0.4 (7.2%) |
| $N^3$-edT | 77.2 ± 2.4 (3.1%) | 81.8 ± 2.7 (3.3%) | 70.5 ± 0.5 (0.6%) | 76.5 ± 0.07 (7.4%) |
| $O^4$-edT | 8.0 ± 0.7 (8.6%) | 7.9 ± 0.6 (6.5%) | 7.7 ± 0.4 (4.9%) | 7.9 ± 0.02 (1.9%) |

Analysis of Human Leukocyte DNA

The DNA adduct in the white blood cell separated from human blood is quantified, and this is a low intrusive biomarker capable of reflecting the level of DNA damage in human body. Since the DNA adduct content in the blood is lower than other tissues in the body, therefore a high-sensitivity and high-specificity detection method is required to serve as a surrogate to evaluate the level of DNA damage in the tissues.

Figure 6A:
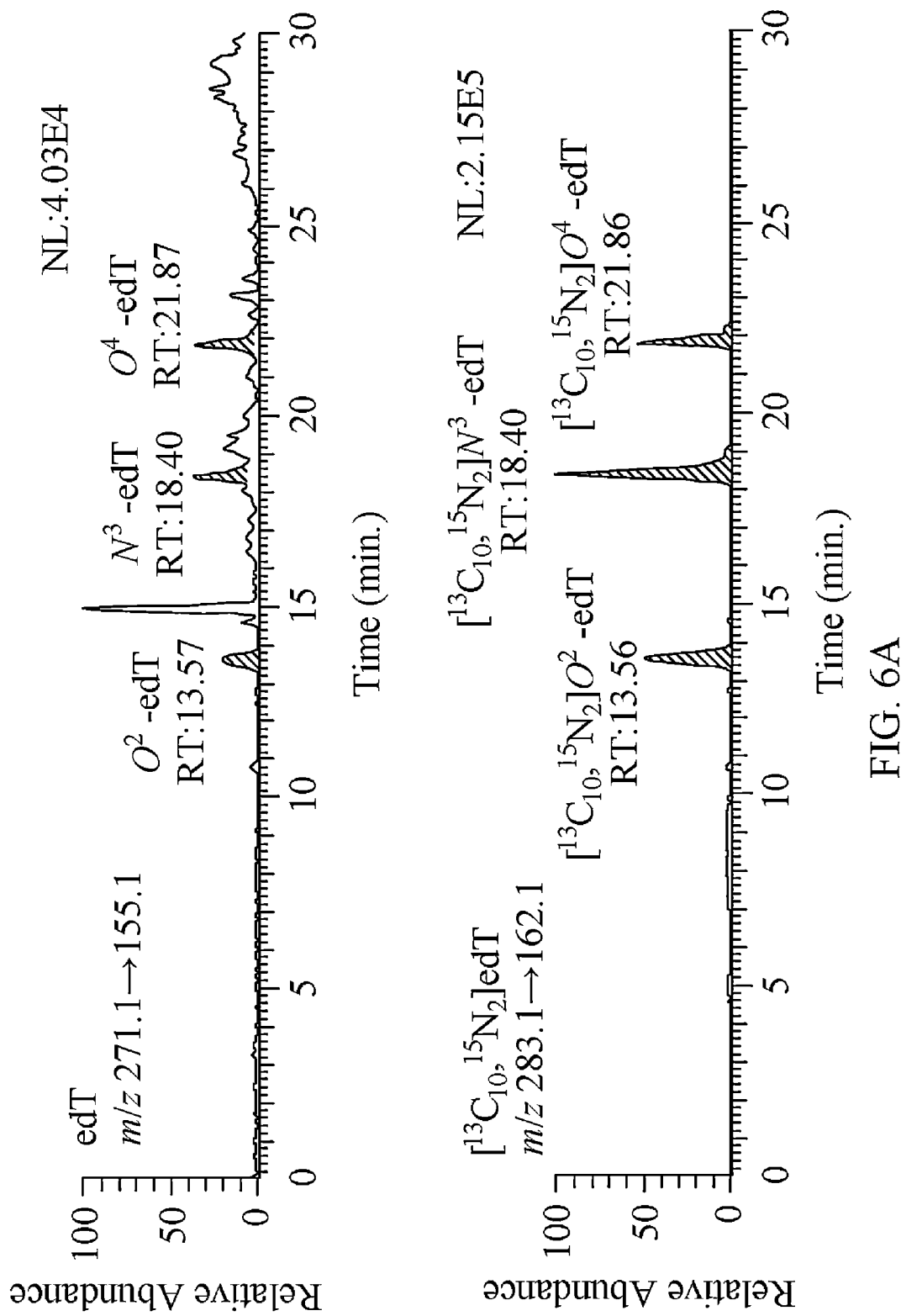
FIGS. 6A and 6B for chromatograms of $O^2$-edT, $N^3$-edT, $O^4$-edT and their isotope-labeled internal standards under the H-SRM mode in accordance with a preferred embodiment of the present invention, respectively.
Figure 6B:
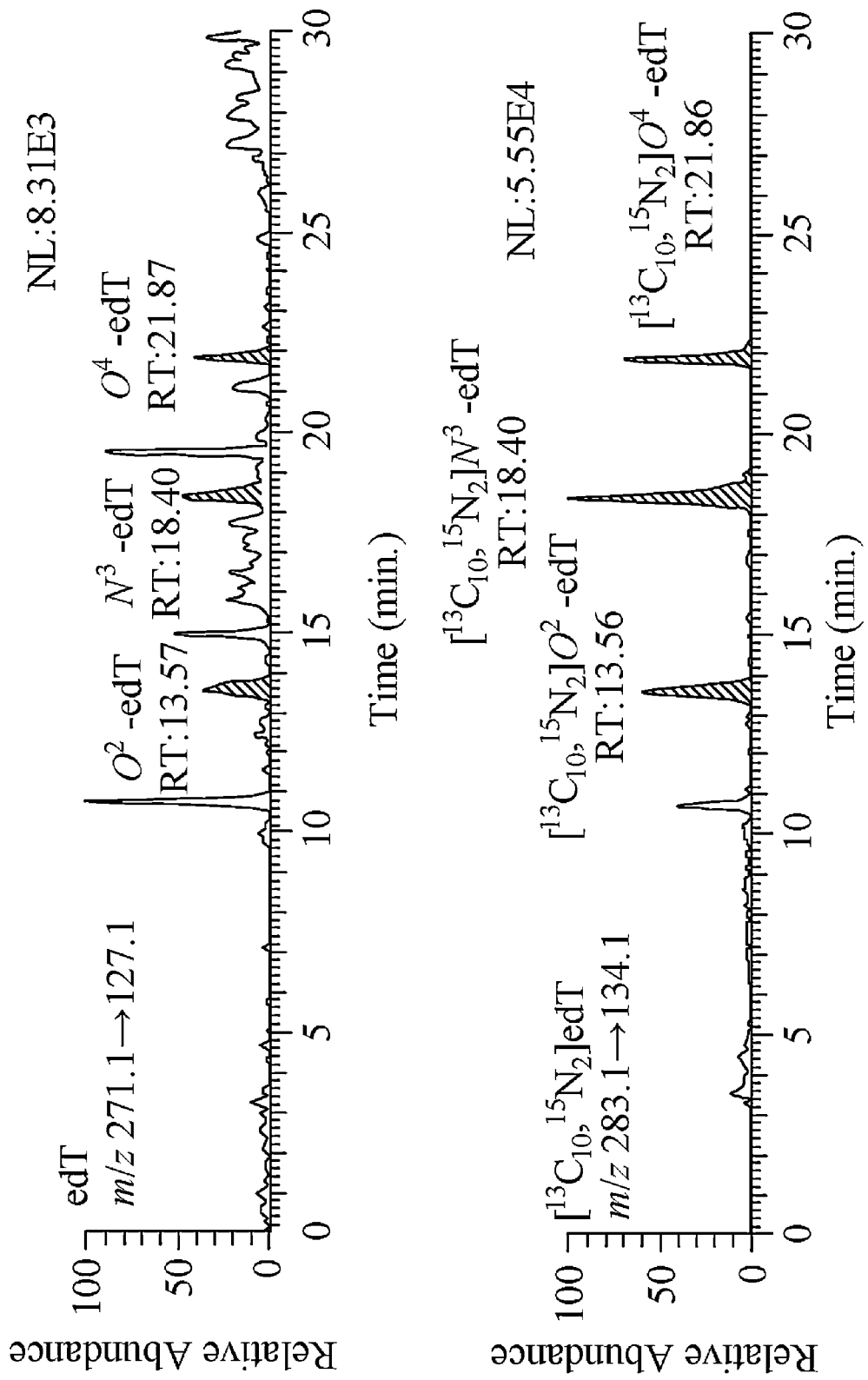

With reference to FIGS. 6A and 6B for chromatograms of $O^2$-edT, $N^3$-edT, $O^4$-edT and their isotope-labeled internal standards under the H-SRM mode in accordance with a preferred embodiment of the present invention, respectively, the three kinds of DNA adducts use Method 1 (as shown in FIG. 6A) and Method 2 (as shown in FIG. 6B) to perform the detection in a highly selective reaction monitoring mode. Although Method 1 has a high sensitivity and can be used for quantifying the DNA adducts, Method 2 can be used as an evidence of the qualitative analysis of the detected DNA adducts of Method 1. In 50 μg of leukocyte DNA, only an amount equivalent to 10 μg of DNA water-soluble matter is injected into the column, and the nanoflow liquid chromatography-nanospray ionization tandem mass spectrometry is used for analysis. The quantities of $O^2$-edT, $N^3$-edT, and $O^4$-edT obtained by using this method for the analysis are 14.8, 13.0 and 30.3 in every $10^8$ normal nucleosides, respectively.

In 40 human white blood cell samples, 5 out of the 20 non-smokers are found to have one or more ethylthymidine adducts. Table 2 summarizes the results of $O^2$-edT, $N^3$-edT and $O^4$-edT detected in the 40 human white blood cell samples by the analysis method of the present invention. Since the DNA adduct contents of smokers and non-smokers are not normally distributed, therefore a nonparametric Mann-Whitney test is used for calculating the statistics. Although the amount of the samples is limited, the average contents of $O^2$-edT, $N^3$-edT and $O^4$-edT in leukocyte DNA of smokers are much higher than those of non-smokers, wherein the p values are equal to 0.0004, 0.0009 and 0.0004, respectively. In the 20 smokers, the average contents of the $O^2$-edT, $N^3$-edT and $O^4$-edT are equal to 44.8±52.0, 41.1±43.8 and 48.3±53.9 in every $10^8$ normal nucleosides. In the 20 non-smokers, the average contents are equal to 0.19±0.87, 4.1±13.3 and 1.0±2.9, respectively. In all samples, the relative standard deviation of each adduct is smaller than 10%, showing that the analysis method of the present invention has excellent reproducibility and precision.

TABLE 2

| Sample | Average Adduct Level (Adduct/$10^8$ nucleosides) ± Standard Deviation (Relative Standard Deviation, %) | | |
|---|---|---|---|
| | $O^2$-edT | $N^3$-edT | $O^4$-edT |
| 1[a] | 1.6 ± 0.02 (1.40%) | 21.8 ± 0.3 (1.40%) | 2.5 ± 0.2 (6.00%) |
| 2[a] | ND[b] | 4.6 ± 0.1 (2.50%) | ND[b] |
| 3[a] | 2.7 ± 0.2 (6.40%) | 3.6 ± 0.3 (8.30%) | 3.0 ± 0.2 (4.60%) |
| 4[a] | 73.4 ± 2.7 (3.60%) | 54.4 ± 5.3 (9.80%) | 68.0 ± 1.8 (2.70%) |
| 5[a] | 5.2 ± 0.1 (2.70%) | 6.0 ± 0.07 (1.20%) | 6.3 ± 0.3 (4.10%) |
| 6[a] | 2.6 ± 0.1 (5.10%) | 1.6 ± 0.07 (4.20%) | 1.6 ± 0.04 (2.30%) |
| 7[a] | 3.8 ± 0.02 (0.60%) | 4.8 ± 0.1 (2.80%) | 3.5 ± 0.2 (5.70%) |
| 8[a] | 6.4 ± 0.2 (2.50%) | 5.2 ± 0.5 (9.50%) | 2.9 ± 0.1 (3.90%) |
| 9[a] | 179 ± 2 (1.30%) | 141 ± 4 (2.60%) | 171 ± 6 (3.30%) |
| 10[a] | ND[b] | 6.11 ± 0.50 (8.20%) | ND[b] |
| 11[a] | 121 ± 3 (2.60%) | 98.8 ± 0.4 (0.40%) | 125 ± 4 (3.40%) |
| 12[a] | 47.8 ± 1.9 (4.00%) | 40.0 ± 3.3 (8.30%) | 52.8 ± 4.4 (8.20%) |
| 13[a] | 26.2 ± 0.8 (3.20%) | 22.3 ± 0.8 (5.10%) | 31.1 ± 2.2 (7.00%) |
| 14[a] | 5.6 ± 0.4 (7.00%) | ND[b] | 2.8 ± 0.3 (9.50%) |
| 15[a] | 43.1 ± 1.1 (2.60%) | 45.2 ± 1.3 (2.90%) | 55.2 ± 1.7 (3.00%) |
| 16[a] | 98.0 ± 3.7 (3.70%) | 95.6 ± 0.4 (0.40%) | 110 ± 2.4 (2.20%) |
| 17[a] | 115 ± 8.4 (7.30%) | 115 ± 2.5 (2.20%) | 141 ± 4.1 (2.90%) |
| 18[a] | 81.5 ± 1.1 (1.30%) | 79.2 ± 4.5 (6.10%) | 84.8 ± 2.9 (3.40%) |
| 19[a] | 69.3 ± 0.3 (0.50%) | 63.7 ± 2.1 (3.20%) | 73.6 ± 1.1 (1.50%) |
| 20[a] | 14.9 ± 1.4 (9.50%) | 13.0 ± 0.4 (3.20%) | 30.3 ± 2.7 (9.00%) |
| 21 | ND[b] | 18.5 ± 1.0 (5.60%) | ND[b] |
| 22 | 3.9 ± 0.2 (4.40%) | 4.7 ± 0.2 (4.80%) | 2.8 ± 0.2 (8.60%) |
| 23 | ND[b] | 57.9 ± 1.9 (3.30%) | 12.5 ± 0.07 (0.60%) |
| 24 | ND[b] | ND[b] | 2.9 ± 0.2 (6.90%) |
| 25 | ND[b] | ND[b] | 2.1 ± 0.1 (6.20%) |
| 26-40 | ND[b] | ND[b] | ND[b] |
| Smoker Mean ± Standard Deviation (n = 20) | 44.8 ± 52.0 | 41.1 ± 43.8 | 48.3 ± 53.9 |
| Non-smoker Mean ± Standard Deviation (n = 20) | 0.19 ± 0.87 | 4.1 ± 13.3 | 1.0 ± 2.9 |

[a]Smoker;
[b]Not detected

In the foregoing research, the $^{32}$P-postlabeling technique can be used for detecting carcinogenic $O^4$-edT in healthy persons' liver, but the contents of $O^4$-edT in healthy persons' leukocytes are not detectable [5]. However, $O^2$-edT and $N^3$-edT in human samples have not been quantified. The analysis method of the present invention can be used for quantifying three kinds of ethylated thymidine DNA adducts, and the contents of the three kinds of ethylated thymidine DNA adducts can be compared in a same leukocyte DNA sample. The three kinds of ethylated thymidine DNA adducts measured in a preferred embodiment of the present invention have significant statistical difference (p<0.0001) in a sample size of 40. Linear regression is used for the calculation, and the correlation coefficients between $O^2$-edT and $O^4$-edT, between $O^2$-edT and $N^3$-edT, and between $N^3$-edT and $O^4$-edT are 0.9896, 0.9840 and 0.9901, respectively. In addition, the average content of $O^2$-edT in smokers has a significant correlation (y=0.4789, p=0.0327) with the smoking index, wherein the smoking index is defined as the number of cigarettes smoked per day multiplied by the smoking time (in year).

What is claimed is:

1. A method of analyzing ethylated thymidine DNA adducts, comprising the steps of:
    providing a leukocyte DNA;
    adding at least one isotope-labeled internal standard and a plurality of enzymes into the leukocyte DNA to hydrolyze the leukocyte DNA into a plurality of nucleosides;
    using a solid phase extraction column to extract the plurality of nucleosides; and
    using an isotope dilution nanoflow liquid chromatography-nanospray ionization tandem mass spectrometry (nanoflow LC-NSI/MS/MS) to detect and quantify at least one ethylated thymidine DNA adduct in the plurality of extracted nucleosides.

2. The method of claim 1, wherein the at least one ethylated thymidine DNA adduct comprises $O^2$-ethylthymidine ($O^2$-edT), $N^3$-ethylthymidine ($N^3$-edT) and $O^4$-ethylthymidine ($O^4$-edT).

3. The method of claim 2, wherein detection limits of $O^2$-ethylthymidine, $N^3$-ethylthymidine and $O^4$-ethylthymidine are equal to 5.0 fg, 10 fg and 10 fg, respectively.

4. The method of claim 2, wherein quantification limits of $O^2$-ethylthymidine, $N^3$-ethylthymidine and $O^4$-ethylthymidine are equal to 50 fg, 100 fg and 100 fg, respectively.

5. The method of claim 2, wherein the at least one isotope-labeled internal standard comprises $[^{13}C_{10},^{15}N_2]O^2$-edT, $[^{13}C_{10},^{15}N_2]N^3$-edT and $[^{13}C_{10},^{15}N_2]O^4$-edT.

6. The method of claim 1, wherein the plurality of enzyme comprises DNase 1, phosphodiesterase I and alkaline phosphatase.

7. The method of claim 1, wherein the isotope dilution nanoflow liquid chromatography-nanospray ionization tandem mass spectrometry has a spray voltage ranging from 1.3 kV to 2.0 kV.

8. The method of claim 1, wherein the isotope dilution nanoflow liquid chromatography-nanospray ionization tandem mass spectrometry has a source temperature ranging from 200° C. to 300° C.

9. The method of claim 1, wherein the isotope dilution nanoflow liquid chromatography-nanospray ionization tandem mass spectrometry further comprises a collision energy ranging from 5 V to 40 V.

10. The method of claim 1, wherein the isotope dilution nanoflow liquid chromatography-nanospray ionization tandem mass spectrometry has an analysis mode which is a highly selective reaction monitoring (H-SRM) mode.

* * * * *